United States Patent [19]
Hastings et al.

[11] Patent Number: 6,117,065
[45] Date of Patent: *Sep. 12, 2000

[54] PERFUSION BALLOON CATHETER WITH RADIOACTIVE SOURCE

[75] Inventors: Roger N. Hastings, Maple Grove; Michael J. Urick, Rogers, both of Minn.

[73] Assignee: SciMed Life Systems, Inc., Maple Grove, Minn.

[ * ] Notice: This patent is subject to a terminal disclaimer.

[21] Appl. No.: 09/103,595

[22] Filed: Jun. 24, 1998

Related U.S. Application Data

[63] Continuation of application No. 08/812,757, Mar. 6, 1997.

[51] Int. Cl.⁷ .................................................. A61M 29/00
[52] U.S. Cl. ................................................................. 600/3
[58] Field of Search ........................... 600/1–8; 604/282; 606/191–194

[56] References Cited

U.S. PATENT DOCUMENTS

| | | |
|---|---|---|
| 2,546,761 | 3/1951 | Loftus . |
| 2,862,108 | 11/1958 | Meilink . |
| 2,955,208 | 10/1960 | Stevens . |
| 3,060,924 | 10/1962 | Rush . |
| 3,147,383 | 9/1964 | Prest . |
| 3,324,847 | 6/1967 | Zoumboulis . |
| 3,505,991 | 4/1970 | Hellerstein et al. . |
| 3,643,096 | 2/1972 | Jeffries, Jr. et al. . |
| 3,669,093 | 6/1972 | Sauerwein et al. . |
| 3,674,006 | 7/1972 | Holmer . |
| 3,750,653 | 8/1973 | Simon . |
| 3,811,426 | 5/1974 | Culver et al. . |
| 3,861,380 | 1/1975 | Chassagne et al. . |
| 3,866,050 | 2/1975 | Whitfield . |
| 3,927,325 | 12/1975 | Hungate et al. . |
| 4,096,862 | 6/1978 | DeLuca . |
| 4,220,864 | 9/1980 | Sauerwein et al. . |
| 4,225,790 | 9/1980 | Parsons, Jr. et al. . |
| 4,244,357 | 1/1981 | Morrison . |
| 4,281,252 | 7/1981 | Parsons, Jr. et al. . |
| 4,314,157 | 2/1982 | Gaines . |
| 4,364,376 | 12/1982 | Bigham . |
| 4,584,991 | 4/1986 | Tokita et al. . |
| 4,588,395 | 5/1986 | Lemelson . |
| 4,631,415 | 12/1986 | Sauerwein et al. . |
| 4,702,228 | 10/1987 | Russell, Jr. et al. . |
| 4,706,652 | 11/1987 | Horowitz . |
| 4,763,642 | 8/1988 | Horowitz . |
| 4,763,671 | 8/1988 | Goffinet . |
| 4,782,834 | 11/1988 | Maguire et al. . |
| 4,784,116 | 11/1988 | Russell, Jr. et al. . |

(List continued on next page.)

FOREIGN PATENT DOCUMENTS

| | | |
|---|---|---|
| 2166915 | 8/1996 | Canada . |
| 0 497 495 A2 | 8/1992 | European Pat. Off. . |
| 0 514 913 A2 | 11/1992 | European Pat. Off. . |
| 0 593 136 A1 | 4/1994 | European Pat. Off. . |
| 0 433 011 B1 | 7/1994 | European Pat. Off. . |

(List continued on next page.)

OTHER PUBLICATIONS

Flexmedics, "Nitinol . . . The Material of Choice for Safter, More Effective Medical Procedures", Copyright 1989, 3 pages.

(List continued on next page.)

*Primary Examiner*—Samuel G. Gilbert
*Attorney, Agent, or Firm*—Crompton, Seager & Tufte, LLC

[57] ABSTRACT

A device for irradiating human vessel interior walls including a perfusion balloon catheter having a radioactive perfusion tube affixed therein. Preferably, the balloon is helical, having adjacent helical strand windings closely spaced in contact upon inflation to minimize trapped blood and reduce attenuation. The perfusion tube can be made radioactive by inclusion of a helical, radioactive metal coil in the perfusion tube wall. In use, the catheter can be advanced over a guide wire to a stenosis, inflated to dilate the site, with beta radiation from the coil passing through the device to the vessel walls, relatively unhindered by blood.

13 Claims, 3 Drawing Sheets

U.S. PATENT DOCUMENTS

| | | | |
|---|---|---|---|
| 4,815,449 | 3/1989 | Horowitz . | |
| 4,819,618 | 4/1989 | Liprie . | |
| 4,851,694 | 7/1989 | Rague et al. . | |
| 4,861,520 | 8/1989 | van't Hooft et al. . | |
| 4,881,937 | 11/1989 | van't Hooft et al. . | |
| 4,897,076 | 1/1990 | Puthawala et al. . | |
| 4,936,823 | 6/1990 | Colvin et al. . | |
| 4,963,128 | 10/1990 | Daniel et al. . | |
| 4,969,863 | 11/1990 | van't Hooft et al. . | |
| 4,976,266 | 12/1990 | Huffman et al. . | |
| 4,976,680 | 12/1990 | Hayman et al. . | |
| 4,976,690 | 12/1990 | Solar et al. . | |
| 5,030,194 | 7/1991 | Van'Hooft . | |
| 5,032,113 | 7/1991 | Burns . | |
| 5,059,166 | 10/1991 | Fischell et al. | 600/3 |
| 5,084,001 | 1/1992 | Van't Hooft et al. . | |
| 5,084,002 | 1/1992 | Liprie . | |
| 5,092,834 | 3/1992 | Bradshaw et al. . | |
| 5,103,395 | 4/1992 | Spako et al. . | |
| 5,106,360 | 4/1992 | Ishiwara et al. . | |
| 5,120,973 | 6/1992 | Rohe et al. . | |
| 5,139,473 | 8/1992 | Bradshaw et al. . | |
| 5,141,487 | 8/1992 | Liprie . | |
| 5,147,282 | 9/1992 | Kan . | |
| 5,163,896 | 11/1992 | Suthanthiran et al. . | |
| 5,176,617 | 1/1993 | Fischell et al. | 600/3 |
| 5,183,455 | 2/1993 | Hayman et al. . | |
| 5,199,939 | 4/1993 | Dake et al. | 600/3 |
| 5,213,561 | 5/1993 | Weinstein et al. | 600/7 |
| 5,267,960 | 12/1993 | Hayman et al. . | |
| 5,279,562 | 1/1994 | Sirhan et al. . | |
| 5,282,781 | 2/1994 | Liprie . | |
| 5,302,168 | 4/1994 | Hess | 600/3 |
| 5,308,356 | 5/1994 | Blackshear, Jr. et al. | 606/194 |
| 5,344,383 | 9/1994 | Liping . | |
| 5,354,257 | 10/1994 | Roubin et al. | 600/7 |
| 5,370,685 | 12/1994 | Stevens . | |
| 5,391,139 | 2/1995 | Edmundson . | |
| 5,405,309 | 4/1995 | Carden, Jr. . | |
| 5,409,015 | 4/1995 | Palermo . | |
| 5,411,466 | 5/1995 | Hess | 600/3 |
| 5,425,720 | 6/1995 | Rogalsky et al. . | |
| 5,429,582 | 7/1995 | Williams . | |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie . | |
| 5,532,122 | 7/1996 | Drukier . | |
| 5,538,494 | 7/1996 | Matsuda . | |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,575,749 | 11/1996 | Liprie . | |
| 5,605,530 | 2/1997 | Fischell et al. | 600/3 |
| 5,611,767 | 3/1997 | Williams . | |
| 5,616,114 | 4/1997 | Thornton et al. | 600/3 |
| 5,618,266 | 4/1997 | Liprie | 604/21 |
| 5,624,372 | 4/1997 | Liprie . | |
| 5,643,171 | 7/1997 | Bradshaw et al. | 600/1 |
| 5,649,924 | 7/1997 | Everett et al. . | |
| 5,653,683 | 8/1997 | D'Andrea . | |
| 5,662,580 | 9/1997 | Bradshaw et al. . | |
| 5,674,177 | 10/1997 | Hehrlein et al. | 600/3 |
| 5,683,345 | 11/1997 | Waksman et al. . | |
| 5,688,220 | 11/1997 | Verin et al. . | |
| 5,707,332 | 1/1998 | Weinberger . | |
| 5,720,717 | 2/1998 | D'Andrea . | |
| 5,722,984 | 3/1998 | Fischell et al. . | |
| 5,728,042 | 3/1998 | Schwager . | |
| 5,728,065 | 3/1998 | Follmer et al. | 606/194 X |
| 5,730,698 | 3/1998 | Fischell et al. . | |
| 5,782,740 | 7/1998 | Schneiderman . | |
| 5,782,742 | 7/1998 | Crocker et al. . | |
| 5,795,286 | 8/1998 | Fischell et al. . | |
| 5,797,948 | 8/1998 | Dunham | 606/194 |
| 5,800,333 | 9/1998 | Liprie . | |
| 5,803,895 | 9/1998 | Kronholz et al. . | |
| 5,807,231 | 9/1998 | Liprie . | |
| 5,816,259 | 10/1998 | Rose . | |
| 5,816,999 | 10/1998 | Bischoff et al. . | |
| 5,820,553 | 10/1998 | Hughes . | |
| 5,833,593 | 11/1998 | Liprie . | |
| 5,840,008 | 11/1998 | Klein et al. . | |
| 5,840,009 | 11/1998 | Fischell et al. . | |
| 5,840,064 | 11/1998 | Liprie . | |
| 5,843,163 | 12/1998 | Wall . | |
| 5,851,171 | 12/1998 | Gasson . | |
| 5,851,172 | 12/1998 | Bueche et al. . | |
| 5,855,546 | 1/1999 | Hastings et al. | 600/3 |
| 5,857,956 | 1/1999 | Liprie . | |
| 5,863,284 | 1/1999 | Klein | 600/3 |
| 5,863,285 | 1/1999 | Coletti . | |
| 5,865,720 | 2/1999 | Hastings et al. . | |
| 5,871,436 | 2/1999 | Eury . | |
| 5,871,437 | 2/1999 | Alt . | |
| 5,873,811 | 2/1999 | Wang et al. . | |
| 5,879,282 | 3/1999 | Fischell et al. . | |
| 5,882,290 | 3/1999 | Kume | 600/3 |
| 5,882,291 | 3/1999 | Bradshaw et al. . | |
| 5,891,091 | 4/1999 | Teirstein . | |
| 5,897,573 | 4/1999 | Rosenthal et al. . | |
| 5,899,882 | 5/1999 | Waksman et al. . | |
| 5,910,101 | 6/1999 | Andrews et al. | 600/3 |

FOREIGN PATENT DOCUMENTS

| | | |
|---|---|---|
| 0 633 041 A1 | 1/1995 | European Pat. Off. . |
| 0 686 342 A1 | 12/1995 | European Pat. Off. . |
| 0 688 580 A1 | 12/1995 | European Pat. Off. . |
| 0 696 906 B1 | 2/1996 | European Pat. Off. . |
| 0 749 764 A1 | 12/1996 | European Pat. Off. . |
| 0 754 472 A2 | 1/1997 | European Pat. Off. . |
| 0 754 473 A2 | 1/1997 | European Pat. Off. . |
| 0 778 051 A1 | 6/1997 | European Pat. Off. . |
| 0 801 961 A2 | 10/1997 | European Pat. Off. . |
| 0 813 894 A2 | 12/1997 | European Pat. Off. . |
| 0 629 380 B1 | 7/1998 | European Pat. Off. . |
| 9102312 U | 8/1992 | Germany . |
| 195 26 680 A1 | 1/1997 | Germany . |
| 197 54 870 A1 | 8/1998 | Germany . |
| 197 24 233 C1 | 12/1998 | Germany . |
| WO 86/03124 | 6/1986 | WIPO . |
| 93/04735 A1 | 3/1993 | WIPO . |
| 94/25106 A1 | 11/1994 | WIPO . |
| 94/26205 A1 | 11/1994 | WIPO . |
| 95/07732 A1 | 3/1995 | WIPO . |
| 95/19807 A1 | 7/1995 | WIPO . |
| 95/26681 A1 | 10/1995 | WIPO . |
| 96/06654 A1 | 3/1996 | WIPO . |
| 96/10436 A1 | 4/1996 | WIPO . |
| 96/13303 A1 | 5/1996 | WIPO . |
| 96/14898 A1 | 5/1996 | WIPO . |
| 96/17654 A1 | 6/1996 | WIPO . |
| 96/22121 A1 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/09937 | 3/1997 | WIPO . |
| WO 97/18012 | 5/1997 | WIPO . |
| WO 97/19706 | 6/1997 | WIPO . |

| | | |
|---|---|---|
| WO 97/25102 | 7/1997 | WIPO . |
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36788 | 8/1998 | WIPO . |
| WO 98/36790 | 8/1998 | WIPO . |
| WO 98/36796 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 98/55179 | 12/1998 | WIPO . |
| WO 98/57706 | 12/1998 | WIPO . |
| WO 99/01179 | 1/1999 | WIPO . |
| WO 99/02219 | 1/1999 | WIPO . |
| WO 99/04706 | 2/1999 | WIPO . |
| WO 99/04856 | 2/1999 | WIPO . |
| WO 99/10045 | 3/1999 | WIPO . |

OTHER PUBLICATIONS

Sutherland, "Managing Cancer Through Synergy", *Administrative Radiology Journal*, Nov. 1996, pp. 21–27.

"*Radiotherapy of Intraocular and Orbital Tumors*," Springer–Verlak publisher, Berlin Heidelberg and New York, copyright 1993, pp. 23–30 and 363–367.

Block, "Peroxygen Compounds, Chapter 9," *Disinfection, Sterilization, and Preservation*, Fourth Edition, Lea & Febiger, Philadelphia, Copyright 1991.

Fackelmann, "Harbinger of a Heart Attack—Does a Protein in the Blood Foretell Heart Trouble," *Science News*, vol. 151, Jun. 14, 1997, pp. 374–375.

Halliwell, "Reactive Oxygen Species in Living Systems—Source: Biochemistry, and Role in Human Disease," Internet Address<http://www.livelinks.com/sumaria/oxy/reactive-.html>, Jul. 21, 1997 from *American Journal of Medicine*, vol. 91, No. 3C, Sep. 30, 1991, p. 14S(9).

Kalli, "Oxygen Emulsion The Question of Free Radicals," Internet Address <http://www.livelinks.com/sumeria/oxy/rad2.html>, Aug. 1, 1997.

Li et al., "Reactive Oxygen Species Induce Apoptosis of Vascular Smooth Muscle Cell," *FEBS Letters*, 404, 1997, pp. 249–252.

Lommatzsch et al., "Radiation Effects on the Optic Nerve Observed After Brachytherapy of Choroidal Melanomas With 106Ru/106Rh Plaques," *Graefe's Arch. Clin. Exp. Ophthalmology*, vol. 232, pp. 482–487, 1994.

Moore, "Free Radial Generation by Thyroid Peroxidase and its Effects on Cells in Vitro," PhD. Dissertation, Group in Endocrinology–University of California Berkeley, California, Dec. 1990.

Raloff, "Nuclear Medicine Gets Friendlier—Experimental Therapies Seek to Poison Just the Disease," *Science News*, vol. 152, Jul. 19, 1997, pp. 40–41.

Tjho–Heslinga et al., "Results of Ruthenium Irradiation of Uveal Melanoma," *Radiotherapy Oncology*, vol. 29, pp. 33–38, 1993.

PERFUSION BALLOON CATHETER WITH RADIOACTIVE SOURCE

CROSS-REFERENCE TO RELATED APPLICATIONS

This application is related to co-pending U.S. Pat. application Ser. No. 08/782,471 pending, filed Jan. 10, 1997, entitled INTRAVASCULAR RADIATION DELIVERY SYSTEM, and to U.S. patent application Ser. No. 08/612,061 abandoned, filed Mar. 7, 1996, entitled PERFUSION BALLOON ANGIOPLASTY CATHETER, the entire disclosures of which are herein incorporated by reference.

FIELD OF THE INVENTION

The invention relates generally to intravascular radiation delivery devices. More specifically, the invention relates to a perfusion catheter having an integral radiation source.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and catheter, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a vessel. The balloon is then inflated and the restriction in the vessel is opened.

Vascular restrictions that have been dilated do not always remain open. In approximately 30% of the cases, a restriction reappears over a period of months. The mechanism of this restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular treatments, including delivery of radioactive radiation have been proposed as a means to prevent or reduce the effects of restenosis. For example, U.S. Pat. No. 5,199,939 to Dake et al. suggests that intravascular delivery of radiation may inhibit restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance for a point source and inversely with distance for a line source laying off center near one vessel wall may significantly overexpose the nearby wall while underexposing the further away wall.

Bradshaw, in PCT publication WO 94/25106, proposes using an inflatable balloon to center the radiation source wire tip. In PCT publication WO 96/14898, Bradshaw et al. propose use of centering balloons which allow blood perfusion around the balloon during treatment. U.S. Pat. No. 5,540,659 to Tierstein suggests use of a helical centering balloon, attached to a catheter at points about the radiation source to allow perfusion past the balloon, between the balloon and radiation ribbon source.

Use of continuous centering balloons having a beta radiation source within significantly attenuates the beta radiation when the balloon is filled with inflation fluid. The balloon may also allow the radiation source to "warp" when placed across curved vessel regions because the design allows the balloon to bend while having the central radiation source lying in a straighter line between the two ends. Segmented centering balloons may improve the warping problem but may also increase beta attenuation by allowing blood to lie or flow between the beta source and vessel walls. Balloons allowing external perfusion in general have the aforementioned beta attenuation problem.

What remains to be provided is an improved apparatus and method for delivering uniform radiation to vessel interiors or walls to inhibit restenosis. What remains to be provided is a device for both dilating and irradiating a vessel wall with a relatively low profile, single device. What would be desirable is a device capable of delivering substantially unattenuated beta radiation with a centered radiation source.

SUMMARY OF THE INVENTION

The present invention provides an improved centering balloon catheter capable of both delivering radiation effectively to vessel walls and performing angioplasty. The delivered radiation is believed to inhibit restenosis following angioplasty.

One embodiment of the present invention includes a catheter having a perfusion head including an inflatable balloon, where the balloon is capable of being inflated with a gas or liquid. The balloon is generally helical, having multiple windings around central shaft portion. The windings are preferably closely spaced longitudinally or in contact with adjacent windings. The perfusion head includes a generally tubular radiation emitting insert or radioactive tube, with the radiation preferably being provided by a beta emitting metal coil forming at least part of the perfusion lumen wall, wherein the perfusion lumen extend longitudinally through the balloon within the central shaft portion inside the balloon windings. Providing a radioactive tube eliminates the need for a radiation delivery device apart from a perfusion balloon catheter. The perfusion tube or tube coil does not greatly increase the profile of the device over that of a non-radiation emitting perfusion balloon catheter. This allows treatment of vessels reachable with the corresponding, non-radioactive perfusion balloon catheter. Use of a tubular radiation source alleviates some of the centering problem associated with point and line sources of radiation, as a tube shaped source is necessarily more geometrically dispersed relative to a wire as the source is in closer proximity to the vessel wall.

The helical balloon of the present invention, in combination with a fixed radiation tube forming, at least in part, the wall of the perfusion lumen, provide improved radiation source centering, as the radiation tube piece-wise approximates any curve the balloon is inflated within, reducing the warping problem. In preferred embodiments, the gas filled interior of the balloon provides relatively unhindered passage of beta radiation emanating from the radioactive tube. This is in contrast to the attenuation of interposing liquid inflation fluid or blood. The present invention helical strand windings having insubstantial space therebetween, also reduces the amount of blood present between windings, which reduces the attenuation of radiation caused by entrapped or perfusing blood around the outside of the balloon.

In use, a catheter embodying the present invention can be inserted through the vasculature of a patient over a guide wire, through the aorta, to a coronary artery site to be treated. In position, the balloon can be inflated with a gas, bringing the balloon surface to bear against the vessel interior wall. In one method, where angioplasty and irradiation are both to be performed together, a high pressure balloon is first inflated with liquid under high pressure, dilating the site. Irradiation of the site can then occur through the liquid filled balloon, however, it is preferable that vacuum be pulled to deflate and empty the balloon, followed by inflating the balloon with a gas during irradiation to reduce attenuation of the source. In another method, where dilatation is not desired, a low or moderate pressure balloon and gas pressure can be used. In this later method, the device can be used for irradiation without angioplasty, for example, after angioplasty has been performed with another device.

DETAILED DESCRIPTION OF THE PREFERRED EMBODIMENTS

Figure 1:
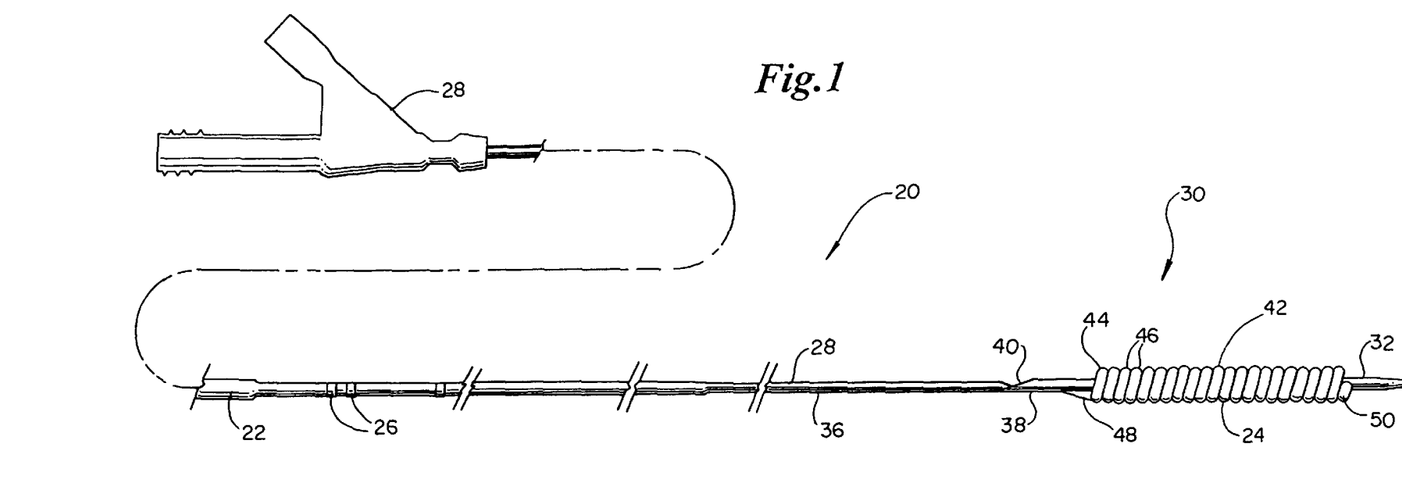
FIG. 1 is a fragmentary side view of catheter according to the present invention.

FIG. 1 illustrates a catheter 20 connected proximally to a manifold 28, having a proximal region 22, a distal region 24, and a distal end 32. A perfusion head 30 includes an inflatable, helical balloon 42 including a strand 44 formed into a series of windings 46 about the longitudinal axis of the catheter 20. Balloon 42 extends from a proximal stem 48 to a distal stem 50. In a preferred embodiment, distal stem 50 is sealed, terminating the balloon. A catheter shaft 28 includes a proximal shaft portion 36 and a distal shaft portion 38. Distal shaft portion 38 includes a skived portion 40 extending distally into a perfusion tube 34 containing a perfusion lumen which extends through balloon 42 within the windings formed by the balloon. Catheter shaft 28 includes a series of marker bands 26.

Figure 2:
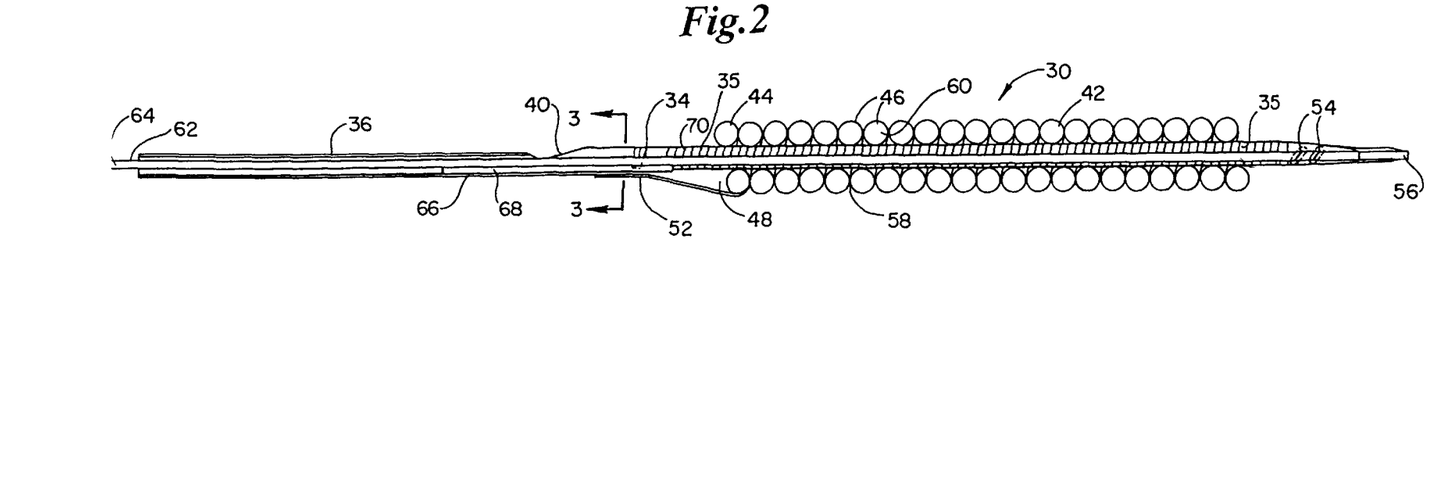
FIG. 2 is an enlarged, longitudinal cross-sectional view of a distal portion of the catheter of FIG. 1.

Referring now to FIG. 2, a cross-sectional view of catheter 20, including distal region 24 is shown in more detail. Proximal shaft 36 is joined to distal shaft 38 with a crimped tube 68. A guide wire tube 62 including a guide wire lumen 64, extends distally through the catheter, exiting catheter 20 at a distal port 56. Surrounding guide wire tube 62 in proximal shaft 36 is an external, proximal inflation lumen 66. In the embodiment of FIG. 2, inflation lumen 66 is external, extending over the length of proximal catheter shaft 36. Balloon 42, having in this embodiment a single strand 44, which is formed into multiple windings 46 has a small interstrand distance indicated at 58. Preferably, adjacent windings are in contact with each other when inflated. Balloon strand 44 is inflatable, having an interior indicated at 60. A preferred embodiment balloon is adapted to be filled with a gas. In one embodiment, balloon 42 is capable of being inflated to the high pressure required for angioplasty. In another embodiment, balloon 42 is adapted to handle only the more moderate pressure required to press the balloon walls against the vessel walls, with that embodiment being used to perform irradiation and not angioplasty. Inflation gas flows distally through proximal inflation lumen 66, through proximal balloon stem waist 52, through proximal balloon stem 48, and into balloon strand interior 60. While the embodiment of FIG. 2 has a single strand, another embodiment has multiple strands, preferably in a side by side configuration.

Perfusion head 30 includes perfusion tube 34 which includes a perfusion lumen 35. The perfusion lumen 35 extends longitudinally through the balloon 42 inside the cylindrical passage formed by the windings. Perfusion blood enters through proximal skived portion 40, flows within perfusion tube 34, exiting distally through distal perfusion ports 54. Blood perfusion allows longer irradiation times than is possible when frequent balloon deflation is required to allow blood flow to downstream arteries and tissue. Perfusion head 30 includes perfusion tube 34 which is necessarily sufficiently strong to maintain an open perfusion channel against the radially inward pressure from inflated balloon 42. The strength is especially important when balloon 42 is to be used for angioplasty. Perfusion head 30 is radioactive. In a preferred embodiment, the radioactivity is contained in the walls of the perfusion lumen, as in the walls of perfusion tube 34. In a preferred embodiment, perfusion tube 34 includes a coil, illustrated as a helical coil 70 in FIG. 2. The preferred embodiment utilizes a metal coil that is a beta radiation emitter.

Figure 3:
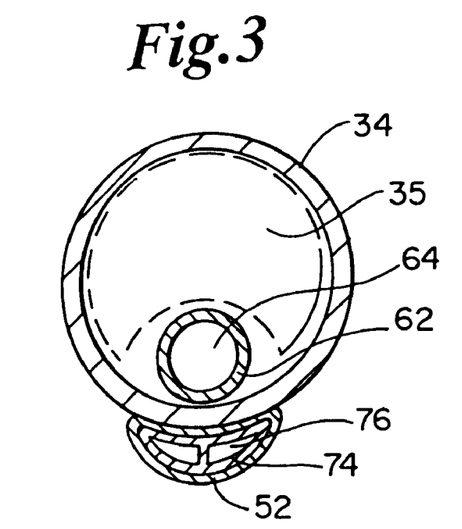
FIG. 3 is an enlarged, cross-sectional view taken through 3—3 in FIG. 2.

Referring now to FIG. 3, a cross-section of the perfusion lumen at 3—3 in FIG. 2 is illustrated. Perfusion tube 34 is illustrated containing a perfusion lumen 35, where coil 70 (not shown in FIG. 3) forms part of the wall of perfusion tube 34. Guide wire tube 62, containing guide wire lumen 64 is illustrated, having a smaller cross-sectional area relative to perfusion lumen 35. Below perfusion tube 34, is a distal inflation tube, with tube 74 defining distal inflation lumen 76. Surrounding or inserted over distal inflation tube 74 is the balloon stem proximal waist 52. In a preferred embodiment, balloon proximal waist 52 is fit over and bonded to inflation tube 74, providing a secure seal against inflation gas under pressure. In one preferred embodiment, the inflation lumen continues proximally as an external lumen for the length of the catheter.

Figure 4:
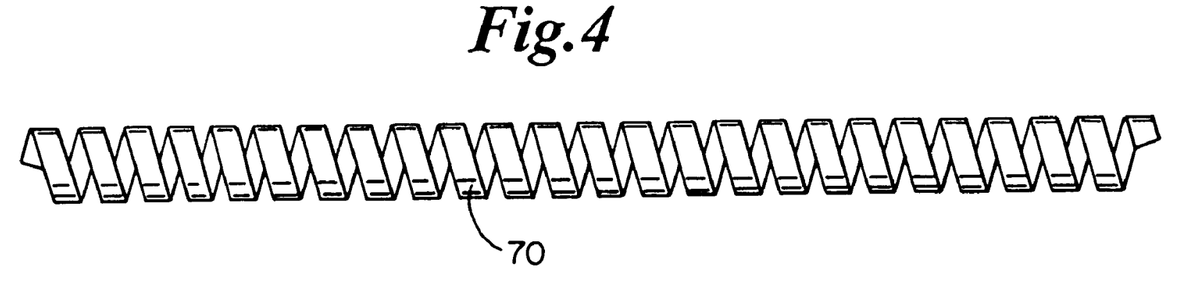
FIG. 4 is an enlarged, side view of a generally tubular radiation emitting coil for inclusion in the perfusion lumen of the catheter of FIG. 2.

Referring now to FIG. 4, perfusion lumen coil 70 is illustrated in detail. In a preferred embodiment, coil 70 is formed of metal and includes a radioactive material. A preferred metal for the coil construction is Nickel-66 or Rhenium-186. One embodiment includes a coil about 25 millimeters in length and about 0.045 inches inside diameter, about 0.048 inches outside diameter. A preferred radioactive material is a beta radiation emitter such as Nickel-66 or Rhenium-186. Beta radiation penetrates tissue only a few millimeters. This is sufficient to penetrate vessel walls and smooth muscle cells, but does not penetrate through the patient and into the operating room, as is possible with gamma emitters. Nickel-66 emits low energy beta radiation and no gamma radiation. Nickel-66 has a half-life of 2.28 days and converts to Copper-66. The Copper-66 emits high energy beta radiation with a half life of 5.10 minutes. The Copper-66 converts to Zinc-66 which is stable and allows disposal by ordinary means within about a month. Nickel-66 can be included in alloys such as Nickel-Titanium, NiTi.

The present angioplasty catheter requires a strong perfusion tube to withstand the pressures of angioplasty. One structure used to reinforce the perfusion lumen is a metal coil. The present invention, by including a metal coil that is radioactive, combines a needed structural perfusion catheter feature with the functionality required to deliver radiation to vessel walls. This is accomplished without an increase in perfusion head cross section, allowing narrowed vessel regions to be treated. Manifold 28 can be formed of polycarbonate, as is well known to those skilled in the art. Catheter shaft 28, including proximal shaft 36 and distal shaft 38 are preferably formed of polyethylene. Balloon 42 and perfusion tube 34 are formed of Polyether Block Amide (PEBA) in a preferred embodiment.

As previously disclosed, the coil of the present invention can be manufactured from a material including nickel. The coil can then be irradiated to convert the material to a Nickel-66 radiation emitting material. With this type of material, it is preferred that the coil be removable from the catheter so that irradiation of the nickel material can take place apart from the balloon dilatation catheter. The present Applicants have disclosed catheter designs having a removable radiation emitting source in patent application Ser. No. 08/812,248, pending entitled "Perfusion Balloon and Radioactive Wire Delivery System", filed on the disclosure of which is incorporated herein by reference. With this embodiment, the coil is carried at the distal end of a shaft having a guide wire lumen extending therethrough. The coil is placed within the perfusion balloon catheter by inserting the shaft within an outside shaft which carries the helical balloon on its distal end.

Figure 5:
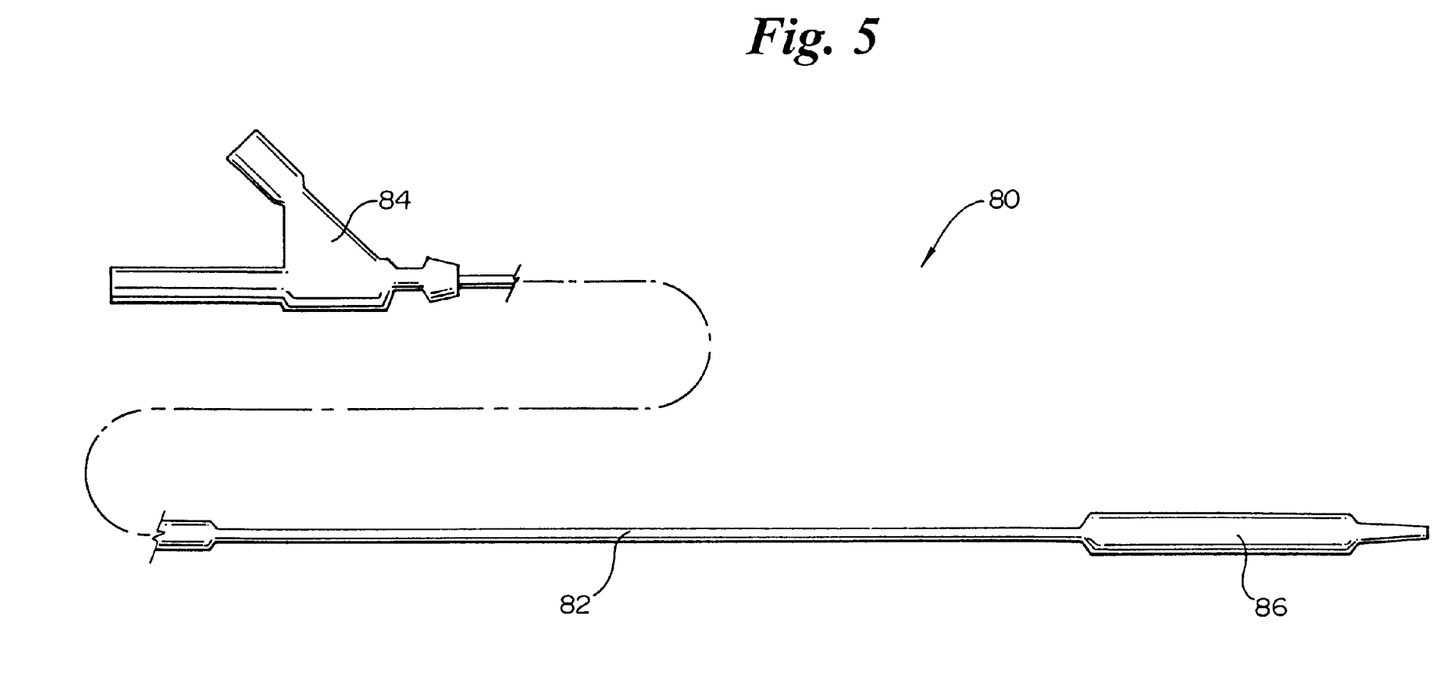
FIG. 5 is a fragmentary side view of a conventional angioplasty catheter for use in combination with the catheter of the present invention.

In use, catheter 20 can be inserted into a patient through the femoral artery, advanced over the aortic arch, and through the ostium of the selected left or right coronary ostium. A preferred method includes first inserting a guide wire, then advancing the catheter over the guide wire. The catheter is advanced to the site of a stenosed vessel region, with the catheter position monitored under fluoroscopy. With the perfusion head of the catheter in position, liquid or gas is supplied to the proximal inflation lumen and the balloon inflated to suitable pressure. A preferred use of the present invention is concurrent radiation exposure and angioplasty. According to this use, high inflation pressure is supplied, sufficient to dilatate the stenosed vessel site. The inflation pressure is maintained, while blood perfuses through the catheter head, reducing the need to cut short the treatment time. In performing angioplasty, use of liquid inflation fluid is preferred, followed by pulling vacuum to deflate the balloon and empty of the fluid. This is followed by inflating the balloon with gas during irradiation to reduce attenuation. In another method, a catheter in accordance with the present invention is used before or after angioplasty, where the angioplasty can be performed with a separate device. For example, a conventional balloon angioplasty catheter 80 as illustrated in FIG. 5 may be used in combination with the catheter of the present invention. Conventional angioplasty catheter 80 includes an elongate shaft 82 having a proximally disposed manifold 84 and a distally disposed angioplasty balloon 86.

While in place with the balloon inflated with gas, the radioactive perfusion tube emits radiation which passes through the gas filled balloon to the vessel walls. In a preferred embodiment, in which the perfusion lumen wall includes a beta emitting radioactive metallic coil, the gas filled balloon provides a path for the beta radiation. The gaseous path does not absorb the beta radiation nearly to the extent of a liquid filled balloon or a blood filled vessel surrounding a catheter. The use of gas thus provides a path favorable for use with beta emitters. This allows use of lower activity radioactive sources relative to those required when beta attenuating blood or liquid inflation fluid is present.

The helical balloon provides improved centering capabilities over a single cylindrical balloon. A cylindrical balloon commonly has a radioactive tube attached at only the opposite balloon end points. When inflated within a vessel curve or bend, this can present a centering problem, as the central tube may take a straighter line between the endpoints, coming too close to one vessel side and too far from the other vessel side. The helical balloon of the present invention, by contacting a radioactive tube over several points, causes the radioactive tube to piece-wise approximate the curve or bend taken by the balloon. Having the helical strands of the balloon substantially in contact or closely adjacent, with substantially no space between the strand windings, provides a clear path through the gas for the beta radiation. Very little blood is trapped between the balloon outside surface and vessel wall. The tight helical balloon design and internal perfusion path provide less opportunity for blood to absorb radiation than a helical design having substantial space between windings and utilizing an external perfusion path.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A device for irradiating vessel walls comprising:
an elongate tubular member having a proximal portion and a distal portion and a radiation source lumen extending therethrough; and
a perfusion head attached to said elongate member distal portion, said perfusion head including an inflatable balloon in fluid communication with an inflation lumen wherein the inflation lumen extends at least to the elongate member proximal portion, said perfusion head having a perfusion tube forming a perfusion lumen separate from said radiation source lumen and extending longitudinally through said balloon; and a radiation source disposed in said radiation source lumen.

2. A device as recited in claim 1, wherein said perfusion tube includes a coiled tubular member affixed within and extending through said balloon to support said perfusion lumen tube during balloon inflation.

3. A device as recited in claim 2, wherein said coiled tubular member includes a radiation emitting material.

4. A device as recited in claim 3, wherein said coiled tubular member is formed of metal.

5. A device as recited in claim 2, wherein said inflatable balloon is formed of a tubular member wrapped around said distal portion of said elongate tubular member to form multiple adjacent windings.

6. A device as recited in claim 5, wherein said inflatable balloon adjacent windings are closely spaced or in contact when inflated to minimize blood trapped between said balloon and a vessel wall to reduce attenuation.

7. A device as recited in claim 5, wherein said centered shaft portion includes said perfusion tube.

8. A method for treating a stenosed vessel site, the method comprising the steps of:
providing a catheter having an elongate member with a proximal portion and a distal portion, and a dilatation head attached to said elongate member distal portion, said dilatation head including an inflatable balloon in fluid lumen indication with an inflation lumen, the inflation lumen extending at least to the elongate member proximal portion, said dilatation head adapted to provide a radiation source that extends longitudinally through at least part of said inflatable balloon;

inserting said catheter into the vasculature of a patient until the inflatable balloon is positioned adjacent to the stenosed vessel site;

inflating the inflatable balloon with a liquid to dilate the vasculature at the stenosed vessel site;

deflating the inflatable balloon;

inflating the inflatable balloon with a gas; and exposing the stenosed vessel site to relatively non-attenuated radiation through said gas-filled inflatable balloon.

9. A method according to claim 8, wherein said dilatation head has a perfusion tube forming a perfusion lumen extending longitudinally through said inflatable balloon.

10. A method according to claim 9, wherein said perfusion tube, at least in part, contains a radiation emitting material.

11. A method according to claim 8, wherein the inflation lumen extends within at least a portion of the elongate member.

12. A method according to claim 8, wherein the inflation lumen extends outside at least a portion of the elongate member.

13. A method for treating a stenosed vessel site comprising the steps of:

providing a balloon dilatation catheter having a dilatation balloon;

providing a radiation catheter having an elongate member with a proximal portion and a distal portion, and a radiation head attached to said elongate member distal portion, said radiation head including a centering balloon in fluid communication with an inflation lumen, the inflation lumen extending at least to the elongate member proximal portion, said radiation head including a radiation source that extends longitudinally through at least part of said centering balloon;

inserting said balloon dilatation catheter into the vasculature of a patient such that the dilatation balloon is positioned adjacent to a treatment site;

inflating the dilatation balloon with a liquid to dilate the treatment site;

deflating the dilatation balloon;

removing the balloon dilatation catheter from the vasculature of the patient;

inserting said radiation catheter into the vascularture of the patient such that the radiation head is positioned adjacent to the treatment site;

inflating said centering balloon with a gas; and exposing said treatment site to radiation from said radiation source through the centering balloon.

* * * * *

UNITED STATES PATENT AND TRADEMARK OFFICE
CERTIFICATE OF CORRECTION

PATENT NO. : 6,117,065
DATED : September 12, 2000
INVENTOR(S) : Hastings et al.

It is certified that error appears in the above-identified patent and that said Letters Patent is hereby corrected as shown below:

Column 6, line 65, after the word fluid delete "lumen indication", insert --communication--.

Signed and Sealed this

Twenty-ninth Day of May, 2001

Attest:

NICHOLAS P. GODICI

Attesting Officer

Acting Director of the United States Patent and Trademark Office